United States Patent [19]

Hirakawa

[11] Patent Number: 4,582,648
[45] Date of Patent: Apr. 15, 1986

[54] α-CYANOACRYLATE COMPOUND, METHOD OF PREPARING SAME AND ADHESIVE COMPRISING SAME

[75] Inventor: Eisuke Hirakawa, Osaka, Japan

[73] Assignee: Kabushiki Kaisha Alpha Giken, Ibaraki, Japan

[21] Appl. No.: 614,899

[22] Filed: May 29, 1984

[30] Foreign Application Priority Data

May 30, 1983 [JP] Japan .................. 58-96735

[51] Int. Cl.$^4$ .................. C07C 121/00; C07C 121/38
[52] U.S. Cl. .................................................. 558/442
[58] Field of Search ...................................... 260/465.4

[56] References Cited

U.S. PATENT DOCUMENTS 2,784,215  3/1957  Joyner ............................. 260/465.4
3,995,641 12/1976  Kronenthal ....................... 128/335

Primary Examiner—Theodore Morris
Attorney, Agent, or Firm—Armstrong, Nikaido, Marmelstein & Kubovcik

[57] ABSTRACT

α-cyanoacrylate compounds expressed by the following general formula:

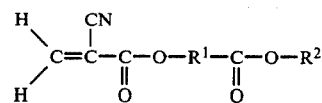

wherein $R^1$ designates —CH$_2$— or

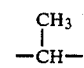

and $R^2$ designates alkyl groups, alkenyl groups or alkynyl groups of $C_1$ to $C_4$. These compounds are preferably synthesized by the reaction of the compounds expressed by the following general formula:

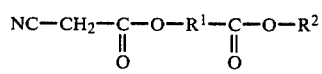

wherein $R^1$ and $R^2$ are same as the above described, with formaldehyde products and then the depolymerization of the resulting dehydrating condensation polymers. These compounds are effectively used as fast-setting adhesives.

2 Claims, 12 Drawing Figures

δ (ppm)

α-CYANOACRYLATE COMPOUND, METHOD OF PREPARING SAME AND ADHESIVE COMPRISING SAME

BACKGROUND OF THE INVENTION

The present invention relates to the novel α-cyanoacrylate compounds, a method of preparing same and adhesives comprising same.

α-cyanoacrylate compounds expressed by the following general formula have been well known as instant adhesives:

Such adhesives are fast set time and put together the substrates made of various kinds of material with each other strongly. α-cyanoacrylate compounds expressed by the above described general formula, in which R is alkoxyalkyl group, halogenated alkyl group, alkenyl group, alkynyl group or the like in addition to alkyl group, have been known. However, almost of them have such disadvantageous that they have an irritating odor whereby being disadvantageous in handling, the circumference of the surfaces bonded being whitened, and the polymerization set products being fragile whereby having lower impact resistance and bending resistance.

It is an object of the present invention to provide novel α-cyanoacrylate compounds.

It is another object of the present invention to provide a novel method of preparing said α-cyanoacrylate compounds.

It is further an object of the present invention to provide novel adhesives comprising same α-cyanoacrylate compounds.

SUMMARY OF THE INVENTION

The inventor of the present invention synthesized various kinds of α-cyanoacrylate compound and investigated their properties and bonding performance to various kinds of substrate (including living bodies). As a result, it was found that the novel α-cyanoacrylate compounds expressed by the following general formula solved the above described disadvantages and had a superior bonding performance.

wherein $R^1$ designates —$CH_2$— or and $R^2$ designates alkyl groups, alkenyl groups or alkynyl groups of $C_1$ to $C_4$.

Said α-cyanoacrylate compounds are preferably prepared by the reaction of the compounds expressed by the following general formula with formaldehyde products and then the thermal depolymerization of the resulting dehydrating condensation polymers:

wherein $R^1$ and $R^2$ are the same as the above described.

DESCRIPTION OF THE INVENTION

The novel α-cyanoacrylate compounds according to the present invention are expressed by the following general formula:

wherein $R^1$ designates —$CH_2$— or and $R^2$ designates alkyl groups, alkenyl groups or alkynyl groups of $C_1$ to $C_4$.

Said compounds are diesters containing two ester parts in one molecule. Concretely speaking, they include
methoxycarbonylmethyl α-cyanoacrylate,
ethoxycarbonylmethyl α-cyanoacrylate,
butoxycarbonylmethyl α-cyanoacrylate,
allyloxycarbonylmethyl α-cyanoacrylate,
propargyloxycarbonylmethyl α-cyanoacrylate,
1-methoxycarbonylethyl α-cyanoacrylate,
1-ethoxycarbonylethyl α-cyanoacrylate,
1-butoxycarbonylethyl α-cyanoacrylate,
1-allyloxycarbonylethyl α-cyanoacrylate and the like.

Olefinic protons of α-cyanoacrylate were commonly observed in the form of single signal at $\delta=7.15$ and $\delta=6.65$ in a $^1$H-NMR spectrum of α-cyanoacrylate compounds expressed by the above described general formula, respectively. Protons of —$CH_2$— put between two ester parts were observed in the form of single signal at δ=4.77 and protons of were observed in the form of quartet signal at δ=5.16 and in the form of doublet signal at δ=1.56. Protons of the end ester part were observed similarly as in usual esters. Chemical shifts, splitting mode and integral ratio of each signal satisfied those for each compound.

The strongest base peak was commonly observed at m/e=80 in their mass spectra. This strongest base peak at m/e=80 was resulted from an ion expressed by the following formula:

In addition, a molecular ion peak M+ of each compound was observed though it was weak. Also fragment ion peaks of each compound, which could be guessed from the splitting mode of the above described structure, were observed.

The absorption of 2240 cm$^{-1}$ resulting from $\nu C\equiv N$, the absorption of 1740 cm$^{-1}$ resulting from $\nu C=O$, the absorption of 3135 cm$^{-1}$ resulting from $\nu C-H$ (olefin) and the absorption of 1620 cm$^{-1}$ resulting from $\nu C=C$ were commonly observed in IR-spectra.

α-cyanoacrylate compounds according to the present invention is preferably synthesized by the reaction of the compounds expressed by the following general formula with formaldehyde products and then the thermal depolymerization of the resulting dehydrating condensation polymers:

wherein $R^1$ and $R^2$ are same as the above described.

Said compounds as raw materials expressed by the above described general formula are obtained by for example the dehydrochloric condensation reaction between cyanoacetic acid and chloroacetates or the dehydrating condensation reaction between cyanoacetic acid and lactates. Said formaldehyde products include formaldehyde and the substances producing formaldehyde in the reaction. However, paraformaldehyde is industrially important.

The reaction of said compounds as raw materials expressed by the above described formula with said formaldehyde products is carried out at a molar ratio of the latter calculated as formaldehyde to the former of for example 0.9 to 1.1:1 in the presence of suitable basic catalysts, for example amines such as piperydine, ethanolamine and diethylamine or basic compounds such as alkaline metal hydroxide and alkaline metal alkoxide in suitable solvents, for example inactive solvents such as benzene, toluene, chloroform and trichloroethylene at 50° to 150° C., preferably 70° to 130° C. to obtain dehydrating condensation polymers. The thermal depolymerization is carried out by washing the resulting compounds as raw materials with water or diluted aqueous solutions of acids and then heating under vacuum at 130° to 250° C., preferably 150° to 220° C. in the presence of suitable depolymerization catalysts such as phosphorus pentoxide, phosphoric acid and condensed phosphoric acid.

The novel α-cyanoacrylate compounds according to the present invention show a bonding performance to a substrate made of various kinds of material in the same manner as the known α-cyanoacrylate such as ethyl α-cyanoacylate and are effectively used as fast setting adhesives. The adhesives comprising the novel α-cyanoacrylate compounds according to the present invention are odorless or slightly give out fragrance whereby being remarkably easy to handle in the preparing process and the bonding process, producing no whitening in the bonding process, and improving the polymerization set products in brittleness. In addition, they are superior to the conventional α-cyanoacrylate in bonding strength to various kinds of substrate, for example metals, plastics, rubber, glass, wood and the like, particularly plated articles. It is perhaps owing to the chelate effect. Furthermore, the adhesives comprising α-cyanoacrylate, in which $R^2$ is allyl group (CH$_2$CH=CH$_2$), of the novel α-cyanoacrylate compounds according to the present invention have such an advantage that the substrate bonded therewith does not show a large reduction in bonding strength even when kept in a long time under the high temperature condition (for example one month at 150° C.). In addition, the adhesives according to the present invention are superior in bonding (i.e. joining, bleed-stopping) strength to tissues of living bodies such as skin, gum, blood vessel and various kinds of organ and absorptivity into tissues after bonding.

Additives such as radical polymerization inhibitors, anion polymerization inhibitors, plasticizers, tackifiers, coloring agents, fillers, diluents, water, perfumes, carboxylic acids, carboxylic anhydrides and polyisocyanates may be added to the adhesives according to circumstances.

The present invention is more particularly described and explained by means of the following Examples, in which "parts" and "%" are all by weight.

EXAMPLE 1

325 parts of ethyl cyanoacetoxyacetate was added drop by drop to the mixture of 65 parts of paraformaldehyde, 350 parts of toluene and 0.4 parts of piperydine put in a four-necked flask provided with a stirrer, a thermometer, a water-separating means and a dropping funnel with heating at 95° to 110° C. and stirring. The reaction was continued with reflux-condensing to drive out the produced water. The stoichiometric amount of water was driven out within two hours and then the reaction mixture was cooled. After cooling the reaction mixture (condensation polymers) was washed with diluted aqueous solutions of acids and then toluene and water contained in the reaction mixture were distilled away under vacuum. Then the depolymerization was carried out by adding 4 parts of phosphorus pentoxide and 2 parts of hydroquinone and heating the resulting mixture under vacuum at 160° to 200° C. to obtain 125 parts of the crude monomer. 82 parts of the purified monomer having a boiling point of 91° to 93° C./0.5 mmHg was obtained by distilling the mixture of the resulting crude monomer, a small amount of phosphorus pentoxide and a small amount of hydroquinone (0.3%, respectively) under vacuum. According to a gas chromatography of its solution diluted with nitromethane, the purity of the resulting purified monomer was 99%. The yield was 23.4%.

The characteristics of the resulting monomer were as follows:

Thus it was confirmed that the resulting monomer was ethoxycarbonylmethyl α-cyanoacrylate (hereinafter reffered to as compound 1) expressed by the following formula:

(molecular weight: 183)

Figure 1:
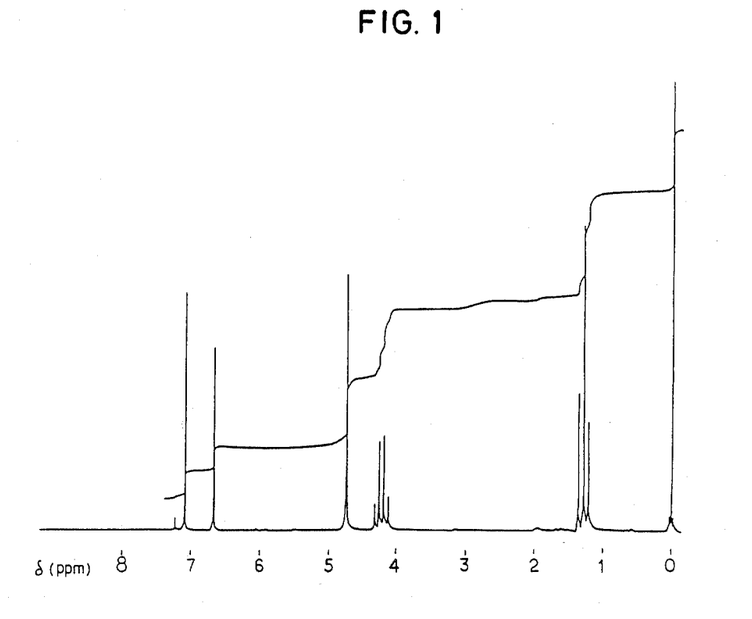
FIG. 1 shows a $^1$H-NMR spectrum of the compound 1 (ethoxycarbonylmethyl α-cyanoacrylate) of the compounds according to the present invention.

(1) $^1$H-NMR spectrum is as shown in FIG. 1 (100 MHz, CDCl$_3$ solvent, TMS internal standard).

Olefinic protons of α-cyanoacrylate were observed in the form of single signal at δ=7.15 and δ=6.65.

Protons of —CH$_2$— put between two ester parts were observed in the form of single signal at δ=4.77.

Figure 2:
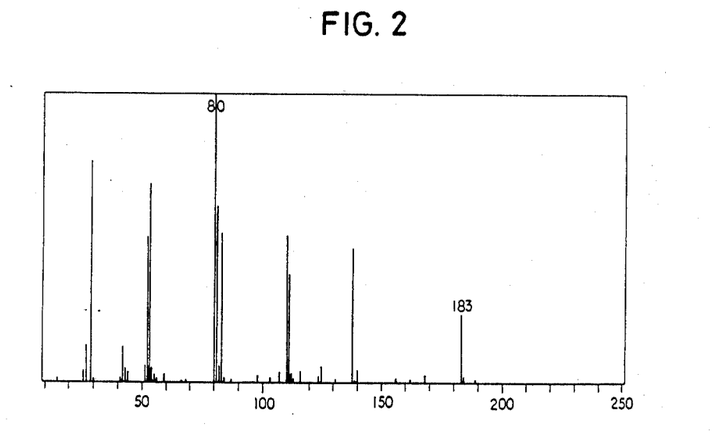
FIG. 2 shows a mass spectrum of said compound 1.

(2) Mass spectrum is as shown in FIG. 2.

The strong peak resulting from a cation expressed by the following formula was observed at m/e=80.

A molecular ion peak M$^+$ was observed at m/e=183.

Figure 3:
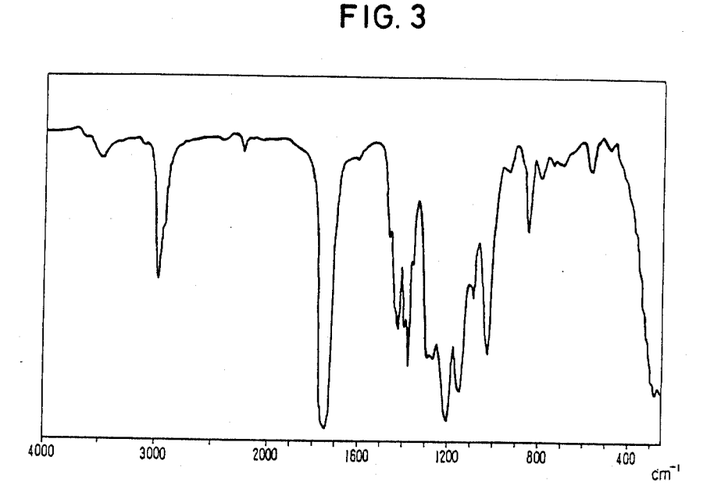
FIG. 3 shows an IR-spectrum of said compound 1.

(3) IR-spectrum is as shown in FIG. 3.

C≡N: Expansion and contraction vibration: 2240 cm$^{-1}$

C=O: Expansion and contraction vibration: 1740 cm$^{-1}$

C—H: (olefin) Expansion and contraction vibration: 3135 cm$^{-1}$

C=C: Expansion and contraction vibration: 1620 cm$^{-1}$ (4) Elementary analysis

|  | Measured value | Theoretical value |
|---|---|---|
| C (%) | 52.66 | 52.46 |
| H (%) | 5.06 | 4.95 |
| N (%) | 8.06 | 7.65 |

(5) Boiling point
91° to 93° C./0.5 mmHg

EXAMPLES 2 TO 5

The compounds 2 to 5 as shown in Table 1 were obtained from paraformaldehyde and methyl cyanoacetoxyacetate, n-butyl cyanoacetoxyacetate, allyl cyanoacetoxyacetate or propargyl cyanoacetoxyacetate, which were the starting materials, in the same manner as in EXAMPLE 1.

Figure 4:
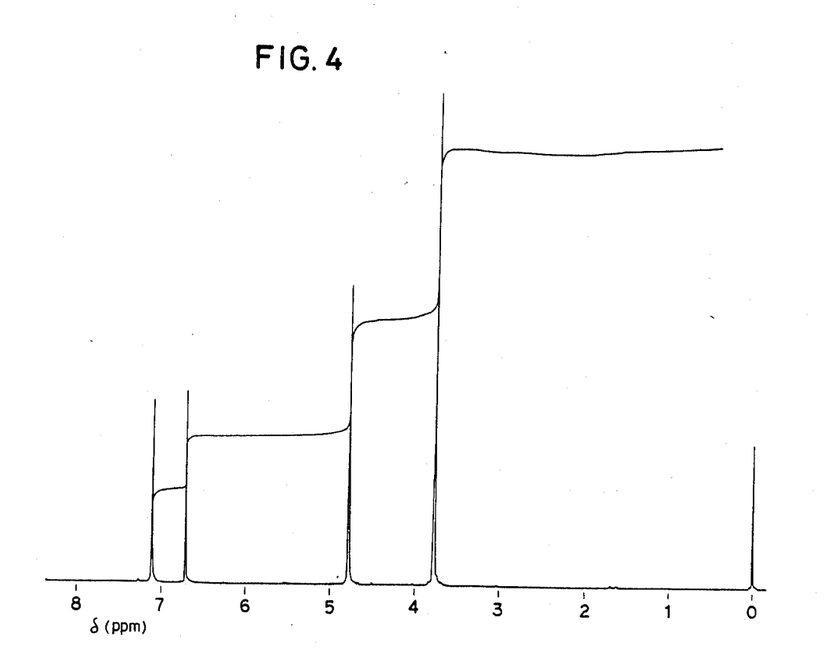
FIG. 4 shows a $^1$H-NMR spectrum of the compound 2 (methoxycarbonylmethyl α-cyanoacrylate) of the compounds according to the present invention.
Figure 5:
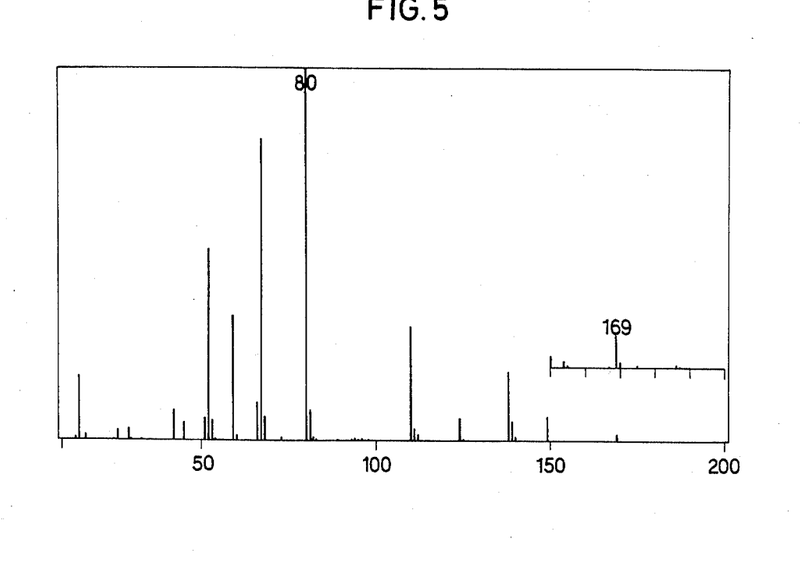
FIG. 5 shows a mass spectrum of said compound 2.
Figure 6:
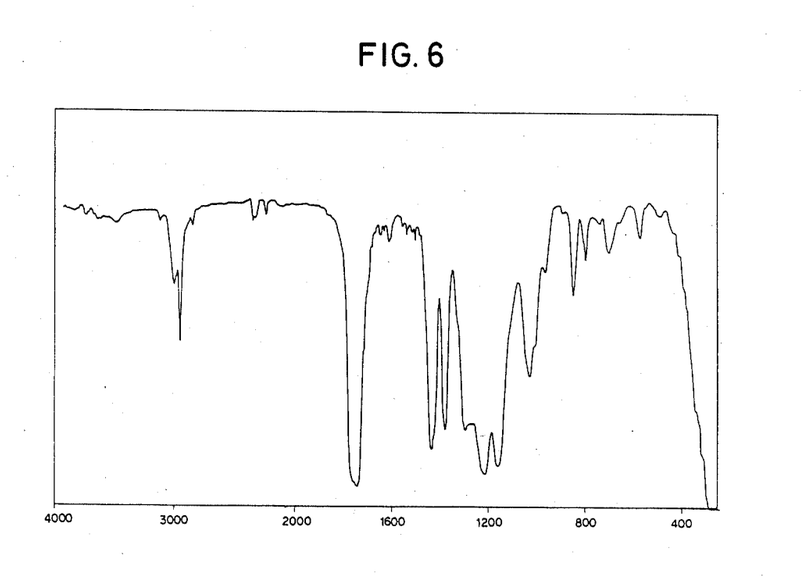
FIG. 6 shows an IR-spectrum of said compound 2.
Figure 7:
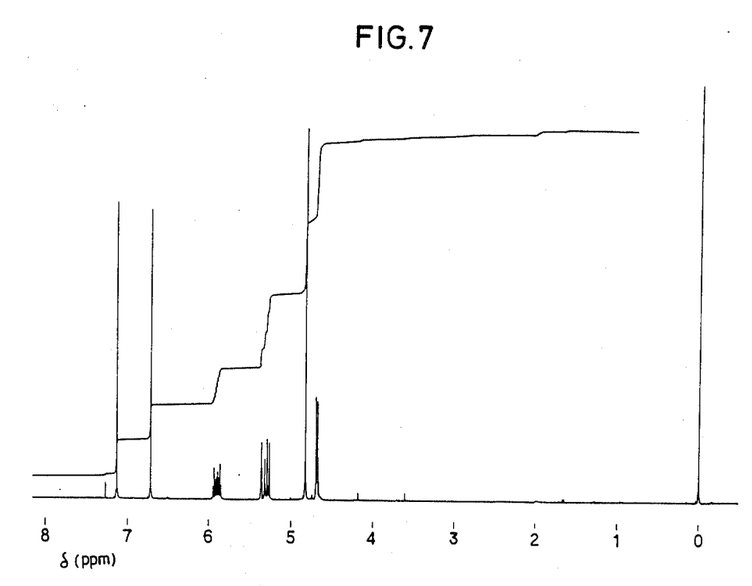
FIG. 7 shows a $^1$H-NMR spectrum of the compound 4 (allyloxycarbonylmethyl α-cyanoacrylate) of the compounds according to the present invention.
Figure 8:
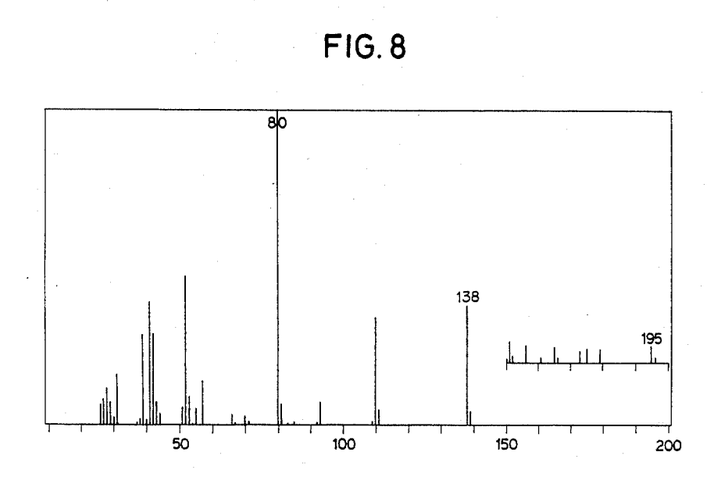
FIG. 8 shows a mass spectrum of said compound 4.
Figure 9:
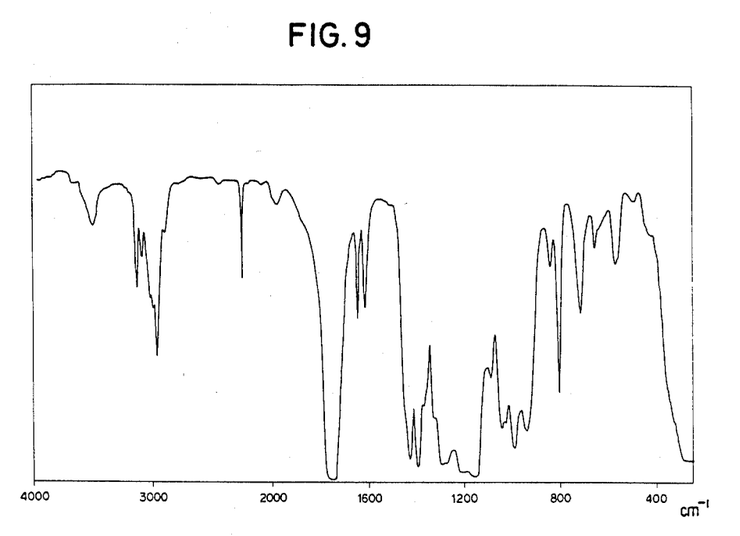
FIG. 9 shows an IR-spectrum of said compound 4.

In addition, $^1$H-NMR spectrum, a mass spectrum and an IR-spectrum of the compound 2 of compounds shown in Table 1, that is to say methoxycarbonylmethyl α-cyanoacrylate (molecular weight: 169) is shown in FIG. 4, FIG. 5 and FIG. 6, respectively. Furthermore, $^1$H-NMR spectrum, a mass spectrum and an IR-spectrum of the compound 4 of compounds shown in Table 1, that is to say allyloxycarbonylmethyl α-cyanoacrylate (molecular weight: 195) is shown in FIG. 7, FIG. 8 and FIG. 9, respectively.

TABLE 1

$$\begin{array}{c} H \\ \diagdown \\ / \\ H \end{array} C=C \begin{array}{c} CN \\ | \\ -C-O-CH_2-C-O-R^2 \\ \| \quad\quad\quad \| \\ O \quad\quad\quad O \end{array}$$

| Compound | R$^2$ | Boiling point | Elementary analysis (%) | | |
|---|---|---|---|---|---|
|  |  |  | C | H | N |
| 2 | CH$_3$ | 89~91° C./0.5 mmHg | 49.93 49.71 | 4.29 4.17 | 8.03 8.28 |
| 3 | CH$_2$CH$_2$CH$_2$CH$_3$ | 113~115° C./0.5 mmHg | 56.56 56.87 | 6.03 6.20 | 6.91 6.63 |
| 4 | CH$_2$CH=CH$_2$ | 101~103° C./0.5 mmHg | 55.07 55.39 | 4.79 4.65 | 7.61 7.18 |
| 5 | CH$_2$C≡CH | 98~100° C./0.5 mmHg | 55.74 55.96 | 3.80 3.65 | 7.62 7.25 |

(Note)
The upper numerical value shows the measured value while the lower numerical value shows the theoretical value in the results of elementary analysis.

EXAMPLE 6

372 parts of ethyl 2-cyanoacetoxypropionate was added drop by drop to the mixture of 75 parts of paraformaldehyde, 350 parts of toluene and 0.5 parts of piperydine put in a four-necked flask provided with a stirrer, a thermometer, a water-separating means and a dropping funnel with heating at 95° to 110° C. and stirring. The reaction was continued with reflux-condensing to drive out the produced water. The stoichiometric amount of water was driven out within two hours and then the reaction mixture was cooled. After cooling the reaction mixture (condensation polymers) was washed with diluted aqueous solutions of acids and then toluene and water contained in the reaction mixture were distilled off under vacuum. Then the depolymerization was carried out by adding 5 parts of phosphorus pentoxide and 3 parts of hydroquinone and heating the resulting mixture under vacuum of 2 to 4 mmHg at 150° to 190° C. to obtain 163 parts of the crude monomer. 122 parts of the purified monomer having a boiling point of 98° to 99° C./1 mmHg was obtained by distilling the mixture of the crude monomer, a small amount of phosphorus pentoxide and a small amount of hydroquinone (0.3%, respectively) under vacuum. The purity of the resulting purified monomer was 98.6%. The yield was 31.7%.

The characteristics of the resulting monomer were as follows:

Thus it was confirmed that the resulting monomer was 1-ethoxycarbonylethyl α-cyanoacrylate (hereinafter referred to as compound 6) expressed by the following formula:

(molecular weight: 197)

Figure 10:
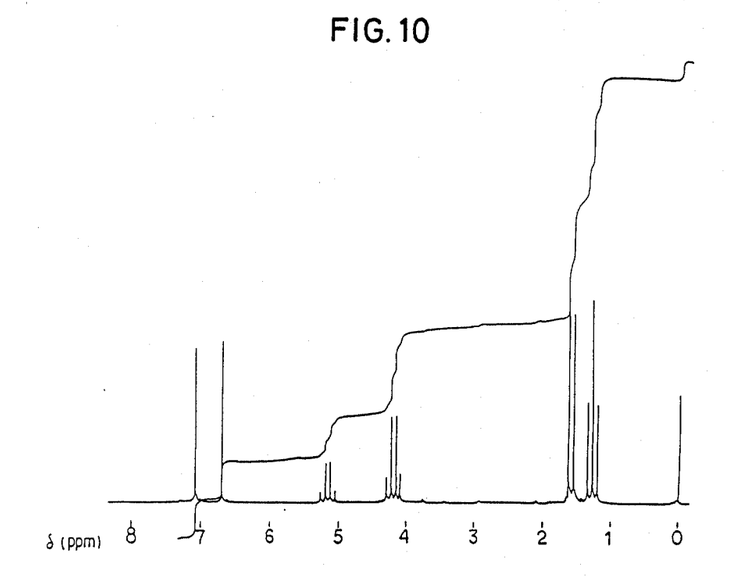
FIG. 10 shows a $^1$H-NMR spectrum of the compound 6 (1-ethoxycarbonylethyl α-cyanoacrylate) of the compounds according to the present invention.

(1) $^1$H-NMR spectrum is as shown in FIG. 10 (100 MHz, CDCl$_3$ solvent, TMS internal standard).

Olefinic protons of α-cyanoacrylate were observed in the form of single signal at δ=7.15 and δ=6.65.

Protons of put between two ester parts were observed in the form of quartet signal at δ=5.16 and in the form of doublet signal at δ=1.56.

Figure 11:
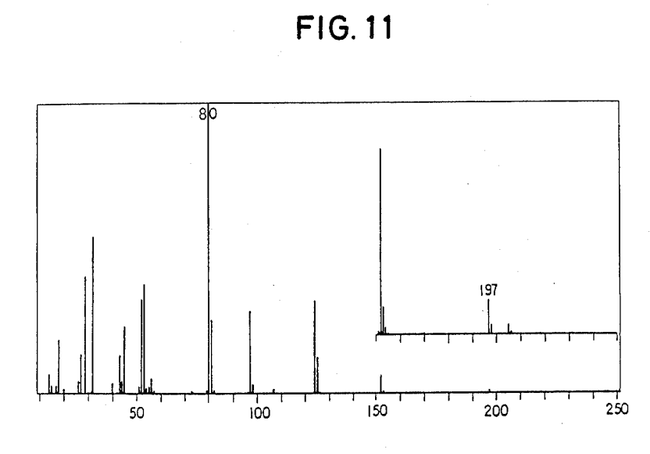
FIG. 11 shows a mass spectrum of said compound 6.

(2) Mass spectrum is as shown in FIG. 11.

The strong peak resulting from a cation expressed by the following formula was observed at m/e=80.

A molecular ion peak M+ was observed at m/e=197.

Figure 12:
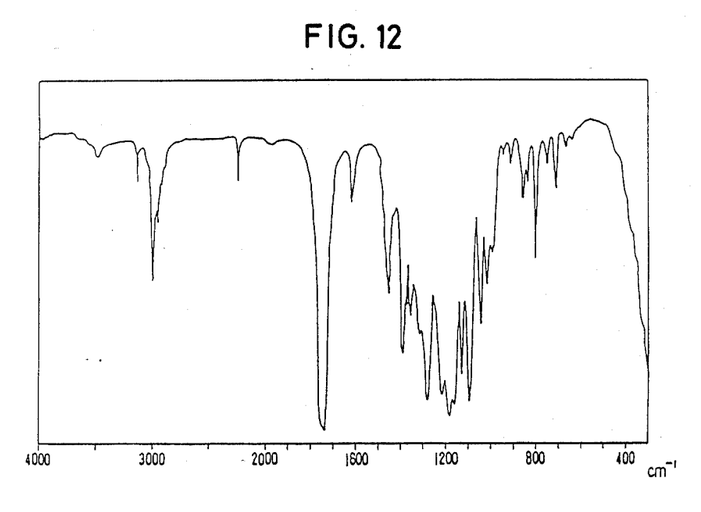
FIG. 12 shows an IR-spectrum of said compound 6.

(3) IR-spectrum is as shown in FIG. 12.

C≡N: Expansion and contraction vibration: 2240 cm$^{-1}$

C=O: Expansion and contraction vibration: 1740 cm$^{-1}$

C—H (olefin): Expansion and contraction vibration: 3135 cm$^{-1}$

C=C: Expansion and contraction vibration: 1620 cm$^{-1}$ (4) Elementary analysis

|  | Measured value | Theoretical value |
|---|---|---|
| C (%) | 54.92 | 54.82 |
| H (%) | 5.69 | 5.62 |
| N (%) | 7.17 | 7.10 |

(5) Boiling point
98° to 99° C./0.5 mmHg

EXAMPLES 7 TO 9

The compounds as shown in Table 2 were obtained from paraformaldehyde and methyl 2-cyanoacetoxypropionate, n-butyl 2-cyanoacetoxypropionate or allyl 2-cyanoacetoxypropionate, which were the starting materials, in the same manner as in EXAMPLE 6.

TABLE 2

$$\begin{array}{c}H\\ \phantom{}\\ H\end{array}\!\!\!\!C\!=\!\!C\!-\!\overset{CN}{\underset{\parallel}{C}}\!-\!O\!-\!CH\!-\!\overset{CH_3}{\underset{\parallel}{C}}\!-\!O\!-\!R^2$$

| Compound | R² | Boiling point | Elementary analysis (%) C | H | N |
|---|---|---|---|---|---|
| 7 | CH₃ | 96~98° C./ 1 mmHg | 52.31 / 52.46 | 5.08 / 4.95 | 7.88 / 7.65 |
| 8 | CH₂CH₂CH₂CH₃ | 114~116° C./ 1 mmHg | 58.79 / 58.66 | 6.90 / 6.71 | 6.60 / 6.22 |
| 9 | CH₂CH=CH₂ | 105~106° C./ 1 mmHg | 57.84 / 57.41 | 5.44 / 5.30 | 6.90 / 6.70 |

(Note)
The upper numerical value shows the measured value while the lower numerical value shows the theoretical value in the results of elementary analysis.

EXAMPLE 10

The compounds obtained in the above described EXAMPLE 1 and EXAMPLE 6 were tested on the performance as adhesives. Also ethyl α-cyanoacrylate was tested on the performance as adhesives for COMPARATIVE EXAMPLE. The results are shown in Table 3.

TABLE 3

|  | Compound 1 | Compound 6 | Ethyl α-cyanoacrylate |
|---|---|---|---|
| Odor | Odorless | Slightly giving out fragrance | Giving out strong irritating odor |
| Whitening | None | None | Whitened all over the surface of Petri dish |
| Set time (sec) |  |  |  |
| Fe/Fe | 160 | 190 | 40 |
| NBR/NBR | 70 | 70 | 50 |
| Tensile shear strength (kg/cm²) |  |  |  |
| Fe/Fe | 153 | 154 | 170 |
| SUS/SUS | 162 | 150 | 120 |
| Al/Al | 146 | 140 | 130 |
| Ni—plating/Ni—plating | 152 | 90 | 40 |
| Zn—plating/Zn—plating | 173 | 130 | 120 |
| ABS/ABS | Adherend failure | Adherend failure | Adherend failure |
| NBR/NBR | Adherend failure | Adherend failure | Adherend failure |
| Joining of living body | Good | Good | Good |

Note 1. The odor was tested on the basis of sensual test by five panelers.
Note 2. The whitening of a drop of adhesives fallen in a clean Petri dish was investigated after leaving for twenty-four hours at room temperature.
Note 3. The set time was measured in accordance with JIS K 6861.
Note 4. The tensile shear strength was measured in accordance with JIS K 6850.

Also the compounds 2 to 5 and 7 to 9 obtained in the above described EXAMPLES 2 to 5 and 7 to 9 were tested on the performance in the same manner as in the above described. The compounds 2 to 5 all were odorless while the compounds 7 to 9 all slightly gave out fragrance. The compounds 2 to 5 and 7 to 9 all did not produce the whitening. The compounds 2 to 5 and 7 to 9 all had the tensile shear strength of the same degree as the compound 1 or 6. They showed also the desirable jointability to living bodies.

In addition, an iron-piece/iron-piece bonded with the compound 4 (allyloxycarbonylmethyl α-cyanoacrylate) as adhesives was tested on tensile shear strength at higher temperature of 150° C. The results are shown in Table 4.

However, COMPARATIVE EXAMPLE in Table 4 shows the adhesive of heat-resisting grade on the market which is obtained by adding aromatic carboxylic acids to ethyl α-cyanoacrylate.

It is found from this Table also that the compound 4 is very effectively used as heat-resisting adhesives.

TABLE 4

|  | Compound 4 | COMPARATIVE EXAMPLE |
|---|---|---|
| Tensile shear strength (kg/cm²) |  |  |
| At first | 165 | 170 |
| After leaving for 10 hours at 150° C. | 81 | 65 |
| After leaving for 7 days at 150° C. | 66 | 8 |
| After leaving for 15 days at 150° C. | 75 | — |
| After leaving for 29 days at 150° C. | 82 | — |

What is claimed is:

1. α-cyanoacrylate compounds expressed by the following general formula:

wherein $R^2$ designates alkyl groups or alkenyl groups of $C_2$ to $C_4$.

2. A method of preparing α-cyanoacrylate compounds expressed by the following general formula:

wherein $R^2$ designates alkyl groups or alkenyl groups of $C_2$ to $C_4$, comprising a step for reacting the compounds expressed by the following general formula:

wherein $R^2$ is the same as the above described, with formaldehyde products; and a step for depolymerizing the resulting dehydrating condensation polymers.

* * * * *